(12) United States Patent
Lombardi

(10) Patent No.: US 7,475,782 B2
(45) Date of Patent: Jan. 13, 2009

(54) CONTAINER FOR CONTROLLING ODOR AND SCENT INCIDENT UPON A HUNTER'S CLOTHING STORED PRIOR TO HUNTING

(76) Inventor: James S. Lombardi, 13090 North Rd., Fenton, MI (US) 48430

( * ) Notice: Subject to any disclaimer, the term of this patent is extended or adjusted under 35 U.S.C. 154(b) by 437 days.

(21) Appl. No.: 11/411,372

(22) Filed: Apr. 26, 2006

(65) Prior Publication Data
US 2007/0251390 A1 Nov. 1, 2007

(51) Int. Cl.
B65D 85/18 (2006.01)
(52) U.S. Cl. .................... 206/524.8; 206/278; 190/110; 190/126; 220/324
(58) Field of Classification Search .................... 96/108, 96/148; 220/500, 529, 240, 324, 377, 378; 190/102, 109, 110, 115, 126; 206/524.8, 206/278; 422/5
See application file for complete search history.

(56) References Cited

U.S. PATENT DOCUMENTS

| 2,510,643 | A | * | 6/1950 | Long .......................... 190/28 |
| 2,517,537 | A | * | 8/1950 | Anderegg ...................... 34/74 |
| 4,014,670 | A | * | 3/1977 | Young ......................... 96/108 |
| 5,568,677 | A | * | 10/1996 | Tobin ............................ 27/17 |
| 5,585,107 | A | | 12/1996 | Vickers |
| 5,776,378 | A | | 7/1998 | Knight |
| 5,891,391 | A | | 4/1999 | Fore |
| 6,135,253 | A | | 10/2000 | Weissman et al. |
| 6,202,849 | B1 | | 3/2001 | Graham |
| 6,263,591 | B1 | | 7/2001 | LaPorte |
| 6,499,574 | B1 | | 12/2002 | Anthony |
| 6,510,946 | B2 | | 1/2003 | Gutierrez et al. |
| 6,561,355 | B1 | | 5/2003 | Forbes et al. |
| 6,793,881 | B2 | | 9/2004 | Himes |
| 2003/0152501 | A1 | | 8/2003 | Byrd et al. |
| 2005/0155891 | A1 | | 7/2005 | Chen |
| 2005/0173439 | A1 | | 8/2005 | Chen |

OTHER PUBLICATIONS

Hunters Prostaff.com, Scent E-Vac Box Concept; Publication Date Unknown.
Scentote.com, ScenTote, downloaded Feb. 7, 2006, 3 pages.
Scentote.com, various advertisement copy regarding ScenTote, downloaded Apr. 11, 2006, 4 pages.
Sequoiaoutdoor.com, advertisement, including picture of ScenTote, downloaded Apr. 11, 2006, 2 pages.
Dealerease.net, advertisement, shows picture of a tote box, downloaded Apr. 11, 2006, 2 pages.

* cited by examiner

Primary Examiner—Frank M Lawrence
(74) Attorney, Agent, or Firm—The Weintraub Group, PLC

(57) ABSTRACT

The present invention discloses a container for controlling odor and scent incident upon a hunter's clothing stored prior to hunting to prevent the stored items from contamination with a human scent and as well inhibit human scent on the clothing escaping from the container. The container includes an open-topped housing and a lid removably connectible to the housing to form an enclosed accessible interior chamber. A check valve in communication with the interior chamber is connected to a vacuum pump for withdrawing air and reducing the pressure in said chamber to a value significantly lower than atmospheric pressure. A sheet or liner of activated carbon is disposed within the interior for adsorbing scents. The present container can be used to store household items, bridal accessories and gowns as well as other various and sundry items where odors are to be prevented.

18 Claims, 1 Drawing Sheet

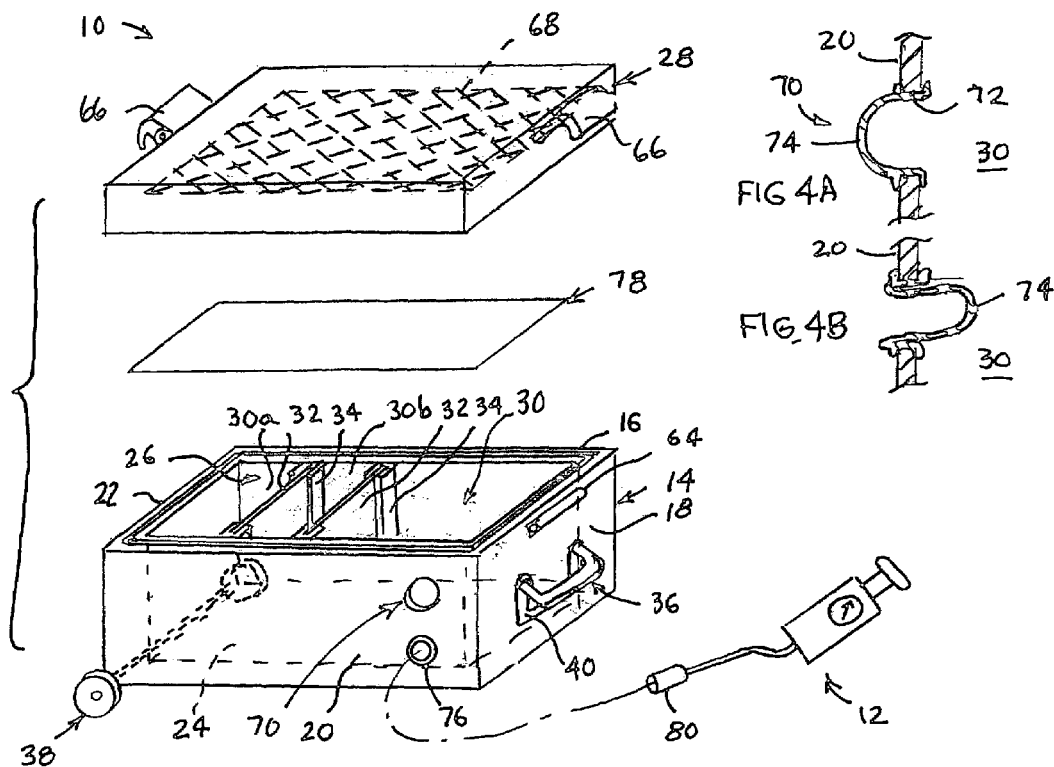
FIG. 1
FIG. 4A
FIG. 4B
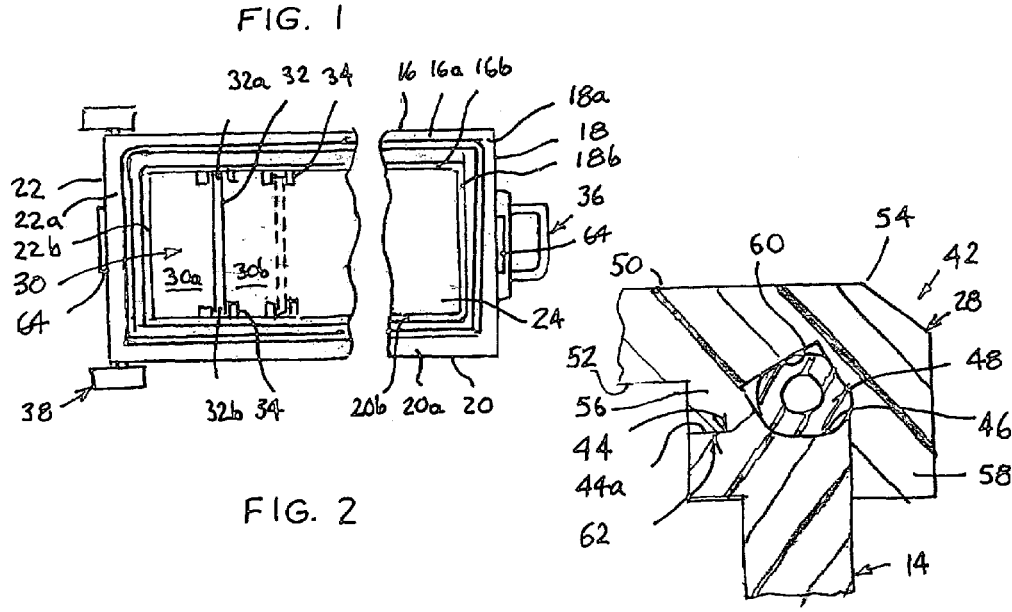
FIG. 2
FIG. 3

CONTAINER FOR CONTROLLING ODOR AND SCENT INCIDENT UPON A HUNTER'S CLOTHING STORED PRIOR TO HUNTING

BACKGROUND OF THE INVENTION

1. Field of the Invention

The present invention pertains to a container for storing and protecting clothing from odor and mildew, such as in the home, or when camping, boating or hunting, and more particularly, to a container for preventing odor and scent incident upon a hunter's clothing stored prior to hunting from contamination with a human scent and as well inhibit human scent on the clothing escaping from the container.

2. Description of the Related Art

Large mammals, such as deer, have well-developed olfactory senses and can sense human odor. Hunters are aware that the clothing they wear might emit odors that can be sensed by the animal they are hunting. As such, special care is taken to make sure that the clothing they wear is not contaminated.

As a first step, special care is taken to rid the clothing from odors normally associated with humans and other sources of odors not typically found in nature. This approach utilizes special scent-free detergents used to wash the clothing, as well as adding a desirable scent to emit a desirable (non-human) odor to cover up the remaining human and unnatural odors.

Notwithstanding, the clothes must still be transported in luggage or garment bags to the hunting venue. Unless protected, the washed and scent-prepared clothing may yet become contaminated with human odor. This may happen during the loading of the storage container. If the container is ineffective to form an airtight seal about the storage area, odors may enter and be absorbed by the clothing. Later, scents or odors may then escape from the container.

Storage bags, luggage, containers and the like have been provided to protect garments worn by hunters from absorbing undesirable odors.

By way of example, U.S. Pat. No. 6,561,355, issued to Forbes et al., discloses a garment bag having an integrated vapor barrier and serially operated zippers separated by a folded zipper separator.

Luggage, storage containers and the like are disclosed in U.S. Pat. No. 6,793,881 to Gutierrez et al.; U.S. Pat. No. 6,263,591 to LaPorte; U.S. Pat. No. 6,135,253 to Weissman et al.; U.S. Pat. No. 5,891,391 to Fore; U.S. Pat. No. 5,585,107 to Vickers and U.S. Pat. Publication Nos. 2005/0155891 to Chen and 2003/0152501 to Byrd et al. Further, U.S. Pat. No. 5,776,378 to Knight is of interest in disclosing method and apparatus for applying scent to clothing.

While each of the above references are believed to have been suitable solutions for the problems desired to be then solved, it is to be appreciated that there is an ongoing need for improvements in containers, enclosures and the like used for controlling odor and scent incident upon a hunter's clothing stored prior to hunting.

SUMMARY OF THE INVENTION

The present invention discloses a container for controlling odor and scent incident upon a hunter's clothing stored prior to hunting to prevent the stored items from contamination with a human scent and as well inhibit human scent on the clothing escaping from the container.

According to a preferred embodiment of this invention, a storage container for storing clothing or equipment used in hunting game and inhibiting odors or scents from passing into the container and contaminating the stored items or escaping from the container and providing game with a human scent warning, comprises housing comprising a bottom wall, a sidewall projecting upwardly from said bottom wall, and a lid removably connectible to the upward extension of said sidewall to form an enclosed accessible interior chamber, first means for connecting and hermetically sealing the connection between the lid and the upward extension of said sidewall to form an airtight seal, said first means operating to prevent scents and odors from enter into and escaping from the interior chamber when the lid is connected to the sidewall, a check valve in communication with said interior chamber, said check valve connectible to a vacuum pump for withdrawing air and reducing the pressure in said chamber to a value significantly lower than atmospheric pressure, second means for indicating if the chamber pressure is lower than atmospheric, and a sheet of activated carbon in said interior chamber for adsorbing scents.

Preferably, the storage container is generally rectangular and formed by opposite pairs of sidewall segments, and at least one divider wall subdivides the interior chamber into two or more compartments whereby to separate the items to be stored from one another. For convenience, the divider walls are removably mounted in channels provided on various of the sidewall segments to enable the size, shape and location of separate storage compartments to be changed, depending on the need.

Importantly, the first means for connecting and hermetically sealing the connection comprises a continuous annular airlock being formed between the upward extension of the sidewall and the lid when the lid is connected to the sidewall, and a continuous seal element in the airlock. The seal element is adapted to be compressed and form an airtight seal that inhibits air from passing into and from the interior chamber upon compressive closure between the lid and the sidewall. In one preferred embodiment, the seal element comprises an elongated continuous cylinder formed of a flattenable elastomeric material, such as provided by a thin walled tube.

Additionally, when the lid is connected to the upward extension of the sidewall, mating end faces and annular grooves of each are juxtaposed with one another, with the annular grooves combining to form the annular airlock, an inner flange of the lid is seated atop a transverse flange or stop of the sidewall, an outer flange of the lid is juxtaposed with the exterior surface of the sidewall, and the seal element is compressed in the airlock to inhibit air passing across the mating faces.

In an aspect according to this embodiment, the first means for connecting and hermetically sealing the connection further comprises a pair of latch receivers on the sidewall and a pair of latches on the lid, the latches being pivotably mounted to the lid for movement between a released position and a latched relation with a respective latch receiver, movement into latching relation substantially simultaneously causing the seal element to be compressed and the lid to be brought into clamped engagement against the upper end face of the sidewall.

In another aspect, the outer flange of the lid may include an engagement surface that is complementary to and adapted to engage the exterior surface of the sidewall when the lid is fitted thereabout. Such fitment may provide frictional closing engagement between the surfaces to enhance air sealing.

Preferably, the storage container includes means for transporting the container, including an axle and wheel assembly provided at one end of the container and a handle assembly provided at the other end portion of the container. The handle assembly includes a shaped recess, and a handle member pivotably mounted for movement between a stored position, held in a compression locked engagement within the shaped recess, and a deployed position, projecting upwardly from the container.

In an aspect of this embodiment, a sheet of netting material is attached to the lower surface of the lid, the sheet of netting defining an accessible pocket against the lower surface for storing items of interest such as maps and the like.

In another aspect of this embodiment, the means for indicating if the chamber pressure is lower than atmospheric comprises a circular opening in the container sidewall, and a thin hemispherical membrane mounted in covering relation to the opening, with the material of the membrane normally biasing the membrane outwardly when the interior chamber pressure is atmospheric. A lower than atmospheric pressure in the interior chamber acts to pull the membrane into the chamber, the membrane acting to restore the membrane to project outwardly when the vacuum is lost.

In yet another aspect of this embodiment, the sheet of activated carbon in the interior chamber is flexible and comprised of a granular material capable of enabling air circulation for adsorbing human odor and scents. If the interior chamber of the container is subdivided into more than one compartment, a separate sheet of activated carbon may be provided for each compartment.

Additionally, the walls and lid of the container may be constructed to include a liner sheet of activated carbon.

Further, in yet another embodiment according to the present invention, this invention is directed to a combination including the container just described, and a portable hand held vacuum pump adapted to be detachably attached to the check valve to suction air from the interior chamber while in the field and in response to the said second means indicating that the interior chamber pressure is not a complete vacuum.

The present invention will be more clearly understood with reference to the accompanying drawings and to the following Detailed Description, in which like reference numerals refer to like parts and where:

BRIEF DESCRIPTION OF THE DRAWINGS

FIG. 1 is a perspective view according to the present invention of a hermetically sealed storage container used in combination with a vacuum pump, the container including a bottom portion for storing clothes and the like and a lid connectible to the bottom portion in a manner to maintain a vacuum in the container.

FIG. 2 is a plan view looking downwardly at the bottom portion of the storage container of FIG. 1 with the lid removed.

FIG. 3 is a section view illustrating the lid when connected in sealed relation to the bottom portion of the container and a seal element providing a sealing closure between mating end faces of the lid and the sidewall of the storage container.

FIGS. 4A and 4B are section views illustrating apparatus for indicating that the container is hermetically sealed and the interior chamber of the container is under a vacuum, with FIG. 4A indicating that the exterior and interior pressures are substantially at atmospheric, and FIG. 4B indicating that the interior pressure is below atmospheric.

DETAILED DESCRIPTION OF THE PREFERRED EMBODIMENT

Turning now to the drawings, FIG. 1 illustrates a portable hunting equipment container 10 for controlling odor and scent incident upon a hunter's clothing stored prior to hunting to prevent the stored items from contamination with a human scent and as well inhibit human scent on the clothing escaping from the container. The container 10 is adapted to be hermetically sealed and the interior placed under a vacuum, such as achieved by the connection to the hand held vacuum pump 12.

The container 10 comprises a generally rectangular box or housing 14 having four sides or sidewalls 16, 18, 20, and 22 which project vertically upwardly from a bottom wall 24 to form a top opening 26 and a closure member or lid 28 adapted to close about the opening and form a closed accessible interior chamber 30 for storing equipment. The housing elements 16-24 and 28 may be of any suitable material and preferably formed of a material that is lightweight, and inexpensive, such as plastic or like polymeric material. Preferably, the bottom wall and sidewalls are integrally molded to one another and form a one-piece container bin.

Generally, when used in hunting, a hunter would prefer that the elements be opaque. However, in other applications, such as where the container is used in the home, the container 10 may be of transparent material wherein to permit the user to see the contents of the housing without removing the lid 28. In either case, the sealing lid closure protects the materials being stored from mildew and, at least as far as the hunter is concerned, prevents expose of the contents to the air and/or possible contamination by exposure to human odors.

The interior chamber 30 may be subdivided into a plurality of separate and separated storage areas 30a, 30b, etc. using a set of panels or divider walls 32 and associated divider channels 34. As shown, the divider channels 34 are disposed on the sidewalls 16 and 20 and extend vertically between the bottom wall 24 and the upper end portion of the respective sidewall. Depending on the application the divider channels 34 are integral with the sidewalls, or separately provided wherein to customize the storage container. The opposite vertically extending lateral edges 32a and 32b of a divider panel 32 register with a respective pair of opposed channels 34 and then slid vertically downwardly in the channels.

The type and number of compartments 30a, 30b, etc. desired in an intended use will determine the size, shape and location of the individual compartments. For example, the hunter may wish to separate boots from certain types of clothing or blankets. In other situations, such as where a hunting bow to be stored might extend between the opposite end walls 18 and 22 of the container, the divider walls 34 might be taken out whereby to form only a single storage area.

The container 10 includes a handle 36 and an axle-wheel arrangement 38 to permit ease of movement and transportability. As shown, the handle 36 is hingedly mounted to the end wall 18 for rotation between stored and in use positions. Preferably, the end wall 18 includes a shaped recess 40 that is complementary to the shape of the handle 36 to receive and retain the handle 36 in a snap fit engagement against the end wall 18 when in the stored position and permit the handle to extend outwardly from the end wall when in the in use position. The axle-wheel arrangement 38 is provided proximate to the intersection between the end wall 22 and the bottom wall or base 24 of the housing 14 to provide rolling movement when the handle is gripped and placed in use.

As best shown by reference to FIG. 3, an airtight seal 42 is formed between the lid 28 and the housing 14 when the lid 28 is placed in closing relation with the housing walls 16, 18, 20, and 22. Although the housing 14 shown is rectangular shaped and formed by four wall segments, a single contoured wall may be used, such as oval or cylindrical in shape, depending on the application.

Shown best in FIG. 2, the upward end portions of the four housing sidewalls 16-22 terminate in a generally planar end face 16a, 18a, 20a, and 22a and include a transverse flange 16b, 18b, 20b, and 22b. The end faces 16a-22a cooperate to form a continuous mating face 44 and the planar faces of the flanges 16b-22b form a continuous stop 44a. Further, a continuous upwardly open channel or groove 46 is provided in the mating face 44 for receiving a continuous tubular seal element 48 inserted therewithin.

The lid 28 has upper and lower surfaces 50 and 52 and an outer periphery 54 that is complementary in shape to the rectangular shape formed by the sidewalls 16-22. Importantly, the outer periphery 54 of the lid 26 is configured to interlock with the upward end portions of the housing sidewalls 16-24 and compress the cross-section of the seal element 48 into airtight sealing relation against and with the mating face 44 of the housing 14.

The outer periphery 54 includes inward and outward flanges 56 and 58 that that project downwardly from the lower surface 52 and form a downwardly open channel 60 that receives and seats atop and about the seal element 48. The inward flange 56 terminates in and forms a continuous mating face 62 that extends 360° and is adapted to be supported atop the stop 44a formed by the planar mating faces of the flanges 16b-22b. The outward flange 58 is continuous, extends 360° and is adapted to be juxtaposed with the upper end portions of the housing sidewalls.

In some applications, the outer flange 58 may form a close friction fit with the exterior surface of the sidewalls 16-22 to increase sealing interengagement between the lid 28 and the housing 14.

The seal element 48 and the annular grooves 46 and 60, in combination with the mating faces, form a continuous annular airlock or air seal between the sidewalls 16-22 and the lid 28 when the lid is closed about and connected to the sidewall. The seal element 48 is adapted to be compressed and form an airtight seal that inhibits air from passing into and from the interior chamber.

Preferably, the seal element 48 comprises an elongated continuous cylinder formed of a flattenable elastomeric material. Further, the cylinder comprises a thin walled tube. In some applications, the seal member 48 may be solid, of compressible elastomeric material, and cylindrical in cross-section.

Further, each end wall 18 and 22 of the storage container 14 is provided with a latch receiver 64 and the opposite ends of the lid 28 are provided with a latch 66. The latch 66 is hinged to the lid 28 for pivoting movement between a released position and a latched relation with a respective latch receiver 64. Movement into latching relation substantially simultaneously causes the seal element 48 to be compressed and the lid 28 to be brought into clamped engagement against the upper end face of the sidewall.

A sheet 68 of netting material is attached to the lower surface 52 of the lid 28. Preferably, the netting sheet 68 is resilient, somewhat yielding, and defines an accessible pocket against the lower surface for storing items of interest such as maps and the like. Generally, the sheet 68 is coextensive with the inner flange 56.

The storage container 10 also includes apparatus 70 for indicating if the pressure in the chamber 30 is lower than atmospheric. Referring to FIGS. 1 and 4A and 4B, the apparatus 70 includes a circular hole or opening 72 in the sidewall 20 and in communication with the chamber 30, and a thin walled, hemispherically shaped membrane 74 of elastomeric material mounted in covering relation with the opening 72.

As illustrated in FIG. 4A, the material of the membrane 74 normally biases the membrane outwardly of the housing 14 when the pressure in the chamber 30 is at or about atmospheric.

As illustrated in FIG. 4B, when the pressure in the chamber 30 is lower than atmospheric, the vacuum pulls the membrane into the chamber 30.

Further, the storage container 10 includes a check valve 76 that is in communication with the interior chamber 30 and connectible to the vacuum pump 12 whereby to enable the vacuum pump to withdraw or suck air from the chamber 30 and reduce the pressure in the chamber to a value significantly lower than atmospheric pressure. Although the check valve 76 is shown placed on the sidewall 20 of the container 10, the valve could be on the lid.

A sheet or carbon liner 78 of activated carbon in disposed in the interior chamber for adsorbing human scents. The carbon liner 78 is flexible and comprises a granular material capable of enabling air circulation and adsorbing human odor and scents.

Additionally, while not shown, the walls and lid of the container may be constructed to include a liner sheet of activated carbon.

Desirably, the hermetic vacuum sealed connection between the seal element 48 with the lid 28 and the sidewalls 16-22 will prevent odors from entering or leaving the interior chamber. Should outside air penetrate the chamber 30, the carbon liner 78 assures that the stored clothing of the hunter is not contaminated. Additionally, the sealed arrangement and carbon liner 78 prevent contaminated air from leaving the chamber 30, thus assuring that an animal will not receive the scent of a hunter.

In use, items to be used in the hunting experience are placed in the housing 14, the lid 28 placed in covering relation atop the housing, and the latches 66 brought into latched relation with the latch receivers 64. The vacuum pump 12 is positioned next to the container 10 and a connector plug 80 of the pump is connected to the check valve 76. During operation of the vacuum pump 12, the pressure in the chamber 30 is lowered and the membrane 74 sucked into the chamber, indicating that the desired vacuum has been achieved.

While the vacuum pump 12 is intended to be temporary, permanent operable connection of a vacuum pump and check valve arrangement may be desirable in some situations.

The invention claimed is:

1. A storage container for storing clothing or equipment to inhibit odors or scents from passing into the container and contaminating the stored items or escaping from the container and providing game with a human scent warning, comprising:
    a housing comprising a bottom wall, a sidewall projecting upwardly from said bottom wall, and a lid removably connectible to the upward extension of said sidewall to form an enclosed accessible interior chamber,
    first means for connecting and hermetically sealing the connection between the lid and the upward extension of said sidewall to form an airtight seal, said first means operating to prevent scents and odors from entering into and escaping from the interior chamber when the lid is connected to the sidewall,
    a check valve in communication with said interior chamber, said check valve connectible to a vacuum pump for withdrawing air and reducing the pressure in said chamber to a value significantly lower than atmospheric pressure, second means for indicating the chamber pressure is lower than atmospheric, and a sheet of activated carbon in said interior chamber for adsorbing scents.

2. The storage container as claimed in claim 1, further comprising a divider wall for subdividing the interior chamber into at least two compartments for storing the stored items in separate compartments.

3. The storage container as claimed in claim 1, wherein said first means comprises:

an continuous annular airlock being formed between the sidewall and the lid when the lid is connected to the sidewall, and a continuous seal element in said airlock, said seal element being adapted to be compressed and form an airtight seal that inhibits air from passing into and from the interior chamber.

4. The storage container as claimed in claim 3, wherein said seal element comprises an elongated continuous cylinder formed of a flattenable elastomeric material.

5. The storage container as claimed in claim 4, wherein said cylinder comprises a thin walled tube.

6. The storage container as claimed in claim 3, wherein the upward extension of said sidewall includes a transverse support flange projecting into the interior chamber, an exterior surface, and a mating end face provided with an annular groove, and, the lid includes an upper and a lower surface, the lower surface forming a mating end face provided with an inner and an outer flange, the flanges projecting from the lower surface of the lid to form an annular groove, wherein when the lid is connected to the upward extension of said sidewall the mating end faces and grooves are juxtaposed with one another, the grooves combine to form the airlock, the inner flange is seated atop the transverse flange of the sidewall, the outer flange is juxtaposed with the exterior surface of the sidewall, and the seal element is compressed in the airlock to inhibit air passing across the mating faces.

7. The storage container as claimed in claim 6, wherein the outer flange projecting from the lower surface of the lid includes an engagement surface, the engagement surface being complementary to and adapted to engage the exterior surface of the sidewall when the lid is fitted thereabout.

8. The storage container as claimed in claim 3, wherein said first means comprises a pair of latch receivers on said sidewall and a pair of latches on said lid, said latches being pivotably mounted to the lid for movement between a released position and a latched relation with a respective latch receiver, movement into latching relation substantially simultaneously causing the seal element to be compressed and the lid to be brought into clamped engagement against the upper end face of the sidewall.

9. The storage container as claimed in claim 1, further wherein said sidewall comprises a plurality of sidewall segments, the sidewall segments extending upwardly from the bottom wall and forming a generally rectangular shape, and a plurality of divider walls, the divider walls dividing the interior chamber into a plurality of separate compartments.

10. The storage container as claimed in claim 9, further comprising third means for removably mounting the divider walls to respective of the sidewall segments to change the size, shape and location of separate storage compartments.

11. The storage compartment as claimed in claim 10, wherein said wall segments have an interior surface, the wall dividers have opposite lateral edges, and said third means comprises a plurality of guide channels, the guide channels extending vertically along the interior surfaces of the wall segments with respective pairs of guide channels being adapted to receive the opposite lateral edges of a wall divider inserted therewithin.

12. The storage container as claimed in claim 1, further wherein said sidewall forms a container having opposite end portions, and further comprising fourth means for transporting the container, said fourth means comprising an axle and wheel assembly provided at one end portion, and a handle assembly provided at the other end portion, the handle assembly including a shaped recess, and a handle member pivotably mounted to said other end portion for movement between a stored position, held in a snap-fit locked engagement within the shaped recess, and a deployed position, projecting upwardly from the container.

13. The storage container as claimed in claim 6, further comprising a sheet of netting material attached to the lower surface of said lid, the sheet of netting defining an accessible pocket against the lower surface for storing items of interest such as maps and the like.

14. The storage container as claimed in claim 1, wherein said second means for indicating the chamber pressure is lower than atmospheric comprises a circular opening in said sidewall, and a thin hemispherical membrane mounted in covering relation with said opening and normally biased outwardly when the chamber pressure is atmospheric, a lower pressure in said chamber pulling the membrane into the chamber when the pressure therein is lower than atmospheric.

15. The storage container as claimed in claim 1, wherein said sidewall and lid are comprised of a rigid polymeric material.

16. The storage container as claimed in claim 15, wherein said polymeric material is transparent.

17. The storage container as claimed in claim 1, wherein said sheet of activated carbon in said interior chamber is flexible and comprises a granular material capable of enabling air circulation for adsorbing human odor and scents.

18. In combination, the container of claim 1, and a portable hand held vacuum pump adapted to be detachably attached to said check valve to suction air from the interior chamber while in the field and in response to the said second means indicating that the interior chamber pressure is not a complete vacuum.

* * * * *